US009265643B2

(12) United States Patent
Britt

(10) Patent No.: US 9,265,643 B2
(45) Date of Patent: Feb. 23, 2016

(54) BLADDER DEVICE AND BRACE APPARATUSES COMPRISING THE BLADDER DEVICE

(71) Applicant: Vernon Britt, Virginia Beach, VA (US)

(72) Inventor: Vernon Britt, Virginia Beach, VA (US)

(73) Assignee: Air Britt LLC, Virginia Beach, VA (US)

( * ) Notice: Subject to any disclaimer, the term of this patent is extended or adjusted under 35 U.S.C. 154(b) by 184 days.

(21) Appl. No.: 13/961,815

(22) Filed: Aug. 7, 2013

(65) Prior Publication Data

US 2014/0052035 A1 Feb. 20, 2014

Related U.S. Application Data

(60) Provisional application No. 61/680,700, filed on Aug. 7, 2012.

(51) Int. Cl.
*A61F 5/00* (2006.01)
*A61F 5/01* (2006.01)
*A61F 7/00* (2006.01)
*A61F 5/058* (2006.01)
*A61F 7/02* (2006.01)

(52) U.S. Cl.
CPC ............ *A61F 5/012* (2013.01); *A61F 5/05816* (2013.01); *A61F 7/00* (2013.01); *A61F 7/02* (2013.01)

(58) Field of Classification Search
CPC ........... A61B 17/1355; A61B 5/02233; A61B 17/1325; A61B 5/024; A61B 5/026; A61B 5/6824; A61B 5/6828; A61B 5/6829; A61B 5/02208; A61B 5/02225; A61B 17/00234; A61B 17/07207; A61B 17/135; B23B 2270/08; B23B 29/03403; B23B 29/03457; B23B 2228/10; B23B 2250/16; B23B 2260/03; B23B 2260/136; B23B 29/03417; B23B 29/03492; B82Y 10/00; B82Y 40/00; G01N 23/225; G01N 21/763; F01C 21/0809; F01C 21/0881; F01C 21/10; F04C 14/04; F04C 14/226; F04C 15/0023; F04C 2/3441; A61F 5/012; A61F 5/05816; A61F 7/00; A61F 7/02; E21B 47/0002; E21B 7/20
USPC .............................. 602/13, 16, 19–28, 60–63
See application file for complete search history.

(56) References Cited

U.S. PATENT DOCUMENTS

| 5,547,461 | A | * | 8/1996 | Levis | 602/19 |
| 2002/0144343 | A1 | * | 10/2002 | Kuiper et al. | 5/81.1 R |
| 2002/0158097 | A1 | * | 10/2002 | Beale | 224/644 |
| 2003/0094474 | A1 | * | 5/2003 | Rotter | 224/662 |

* cited by examiner

*Primary Examiner* — Michael Brown
(74) *Attorney, Agent, or Firm* — Deidre McAuley; McAuley and Associates PLLC

(57) ABSTRACT

Bladder devices and various brace apparatuses are used for providing added support to joint regions of a user. Use of the bladder devices enable a user to control the amount of pressure and resulting support to be supplied to selected portions of the joint regions. The bladder devices are able to be inserted into existing brace apparatuses. In addition, cold/hot packs are also insertable into the brace apparatus along with the bladder devices separately or integrally combined therewith, as needed to provide additional comfort and care to the joint region.

11 Claims, 14 Drawing Sheets

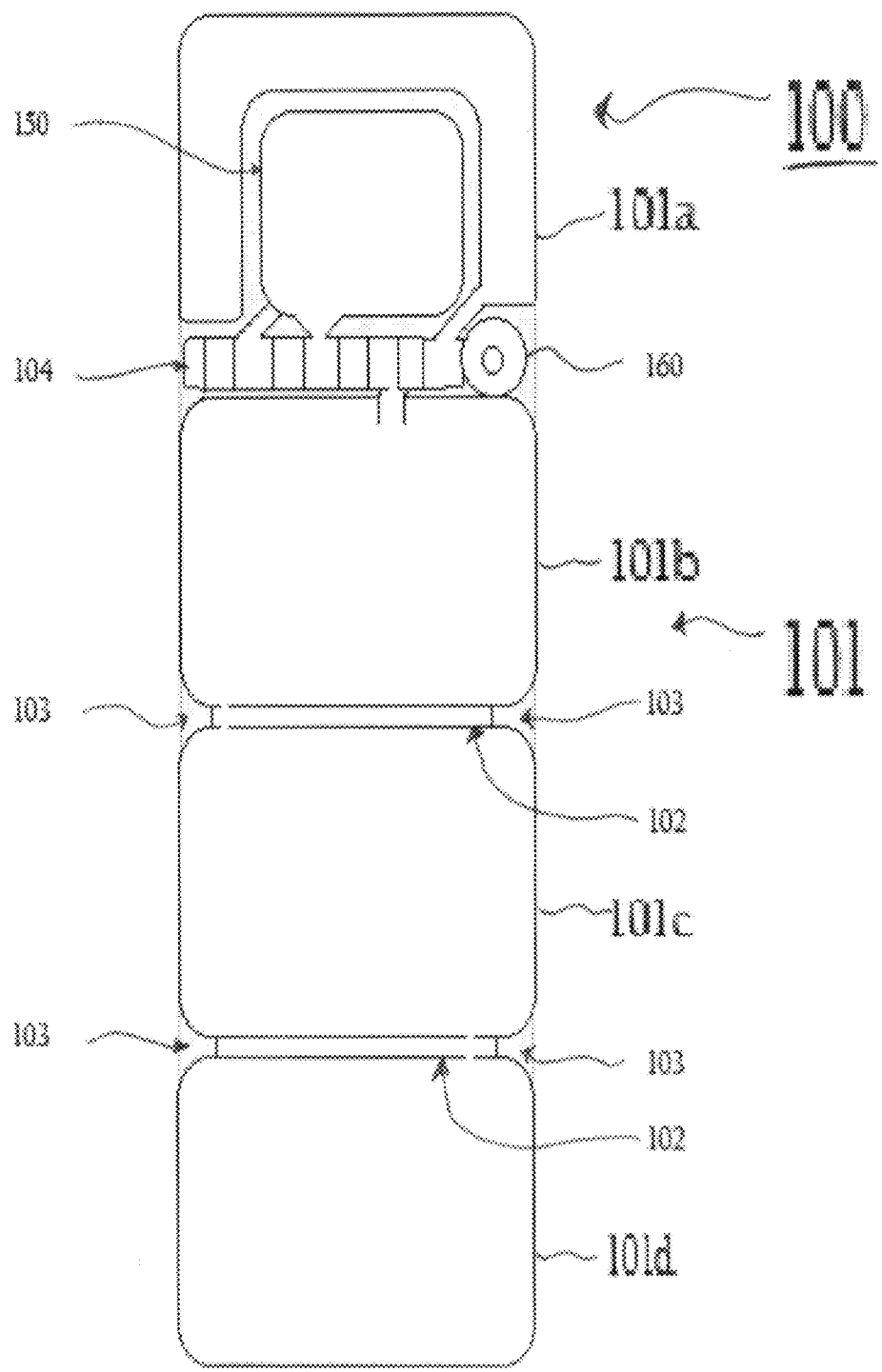

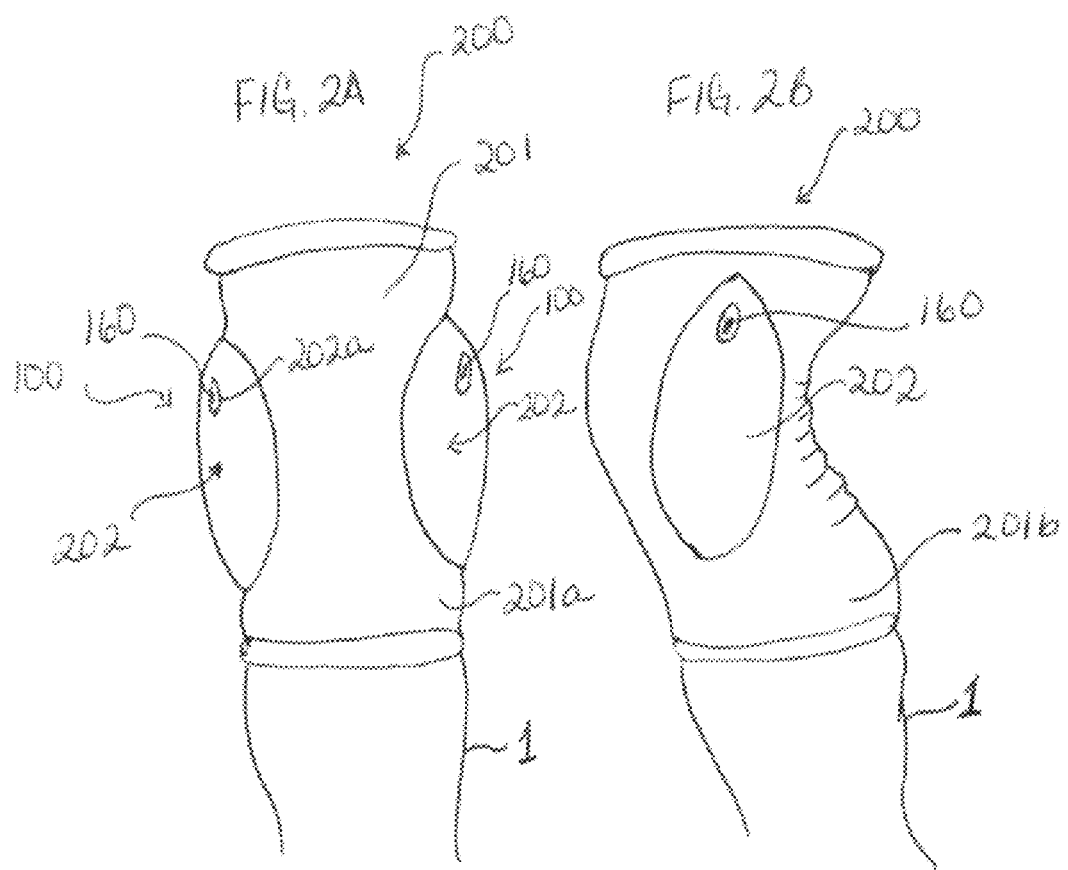

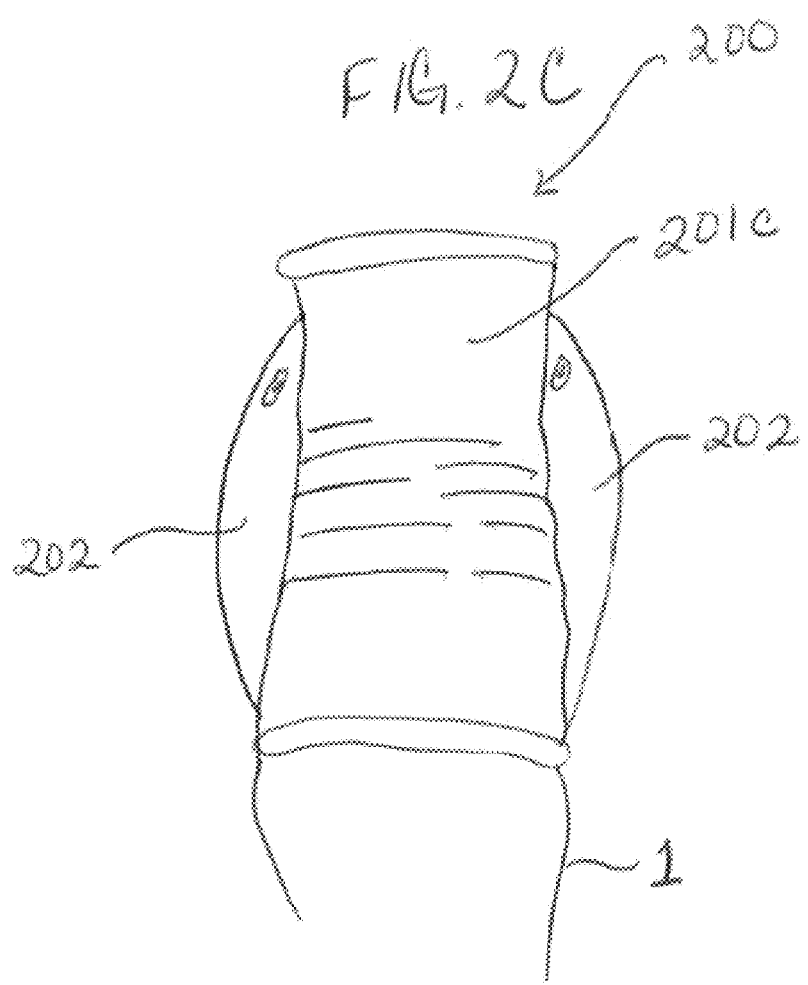

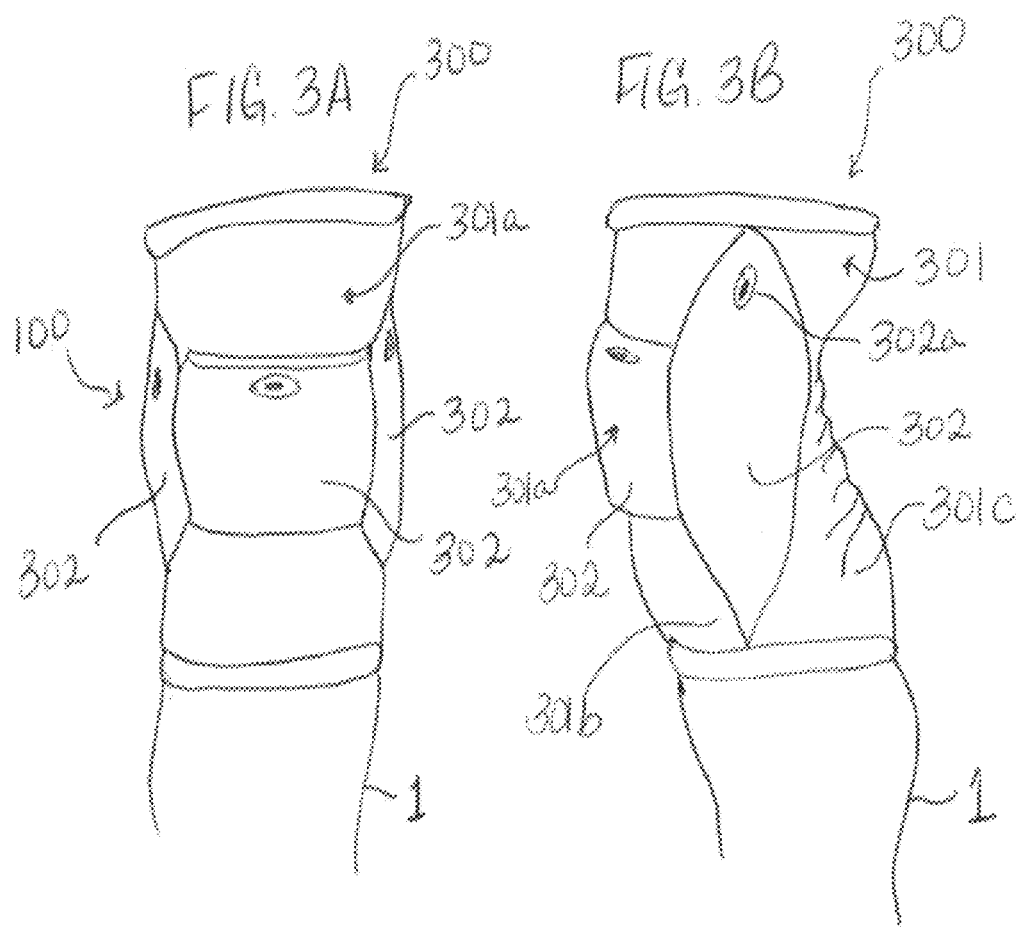

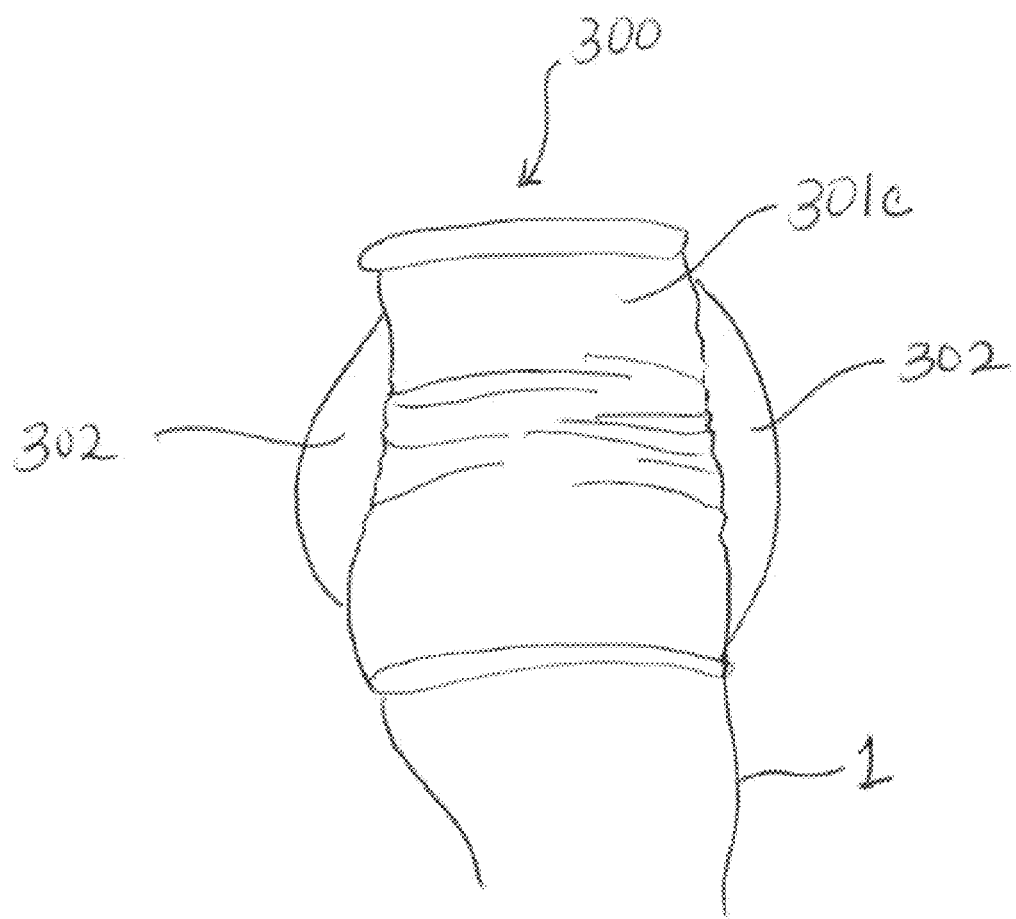

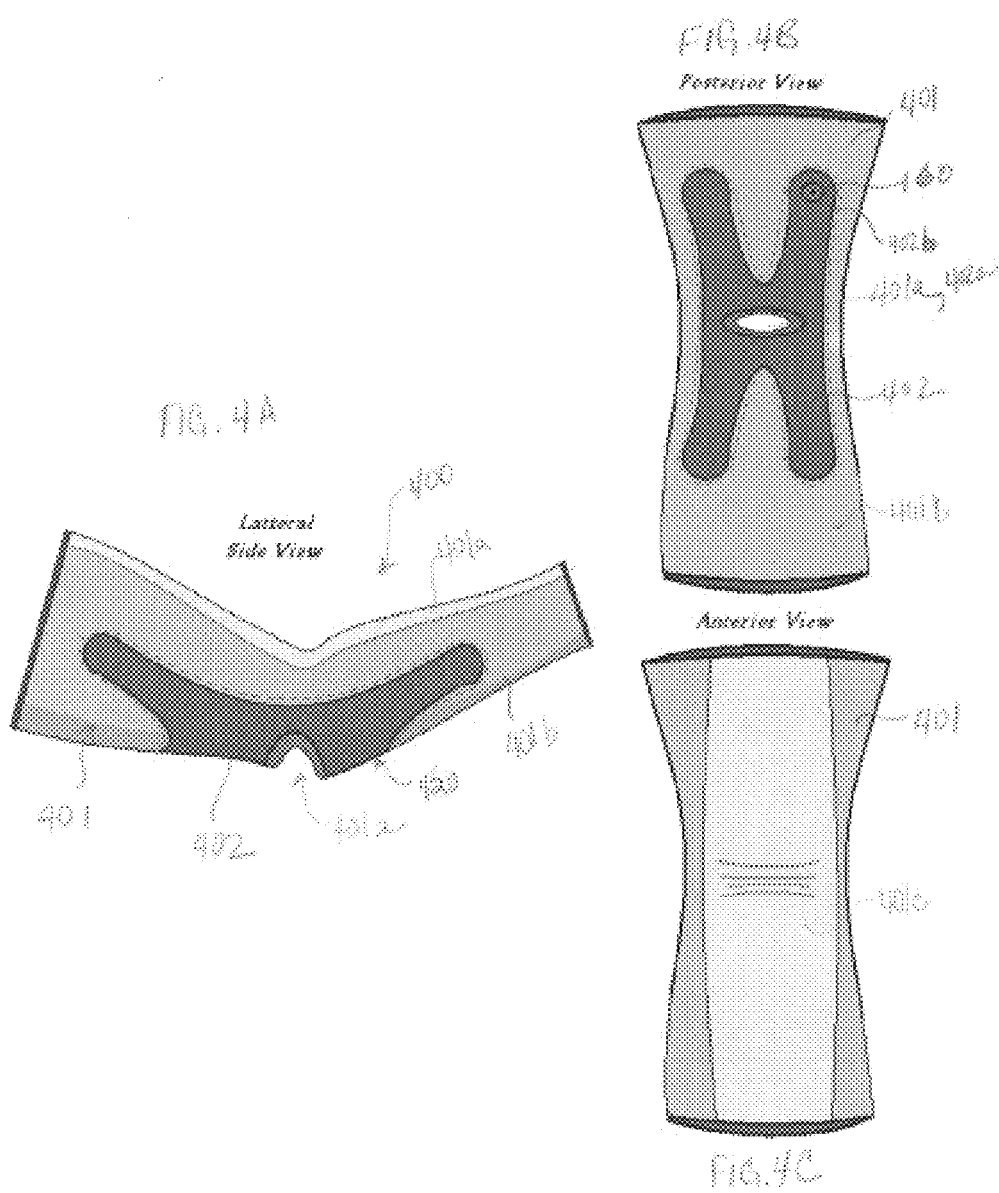

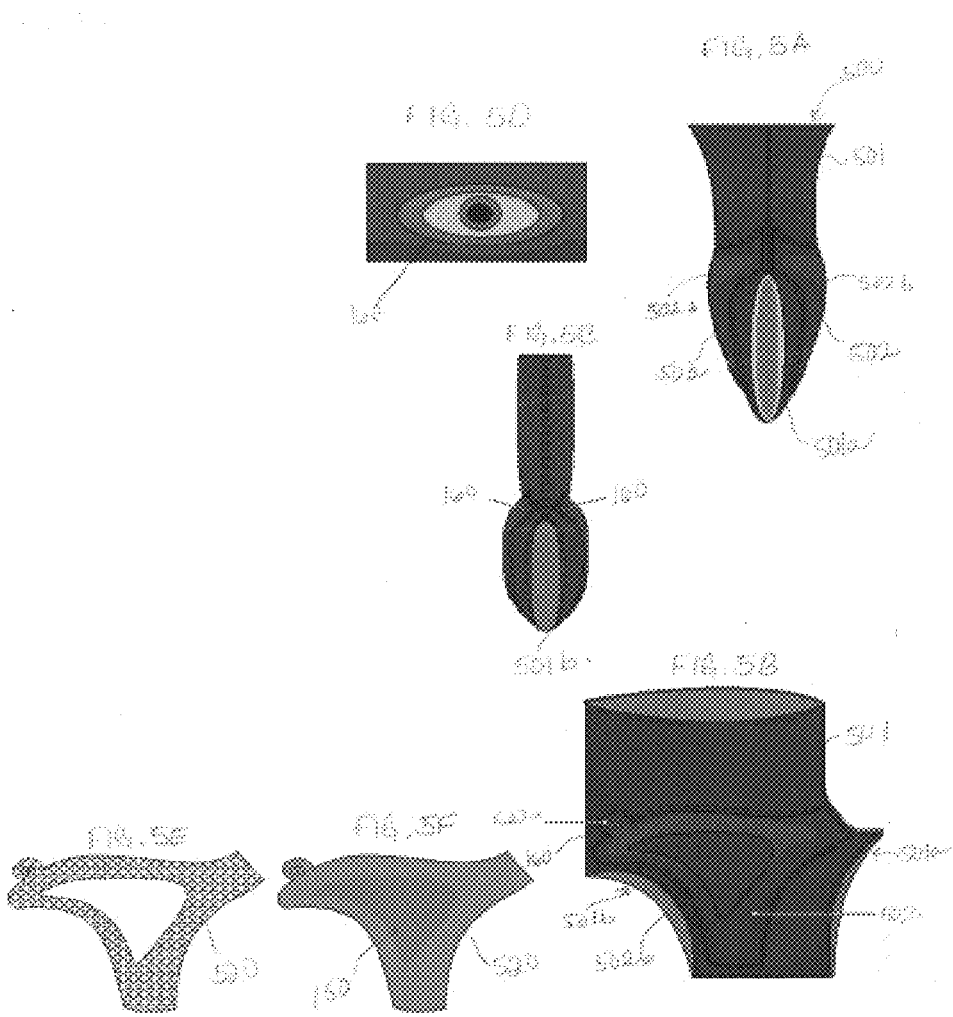

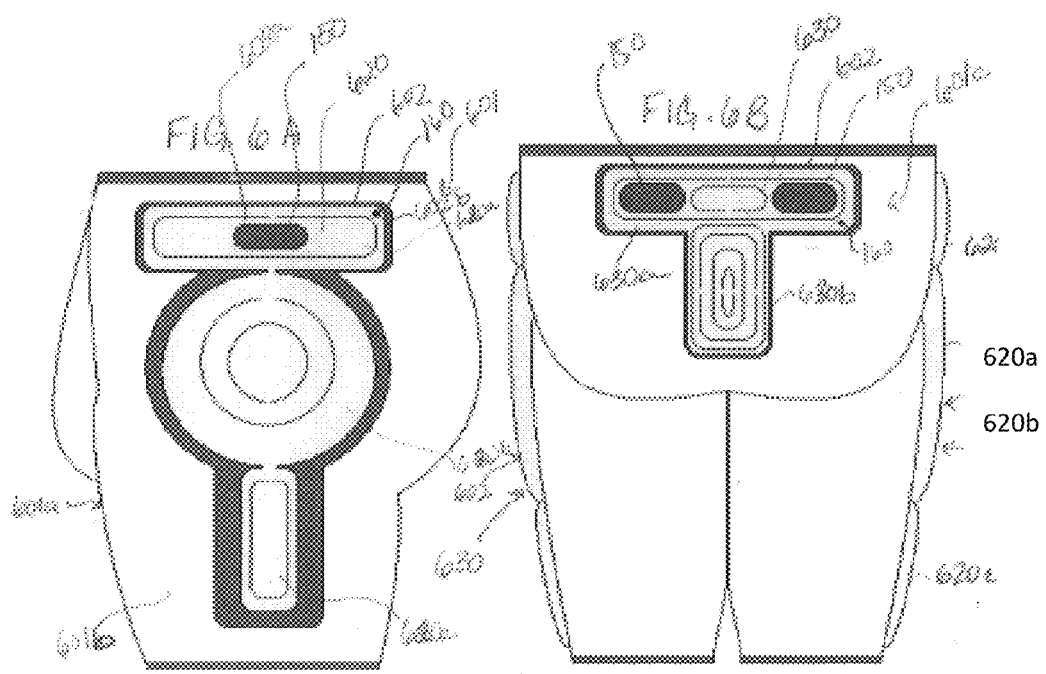

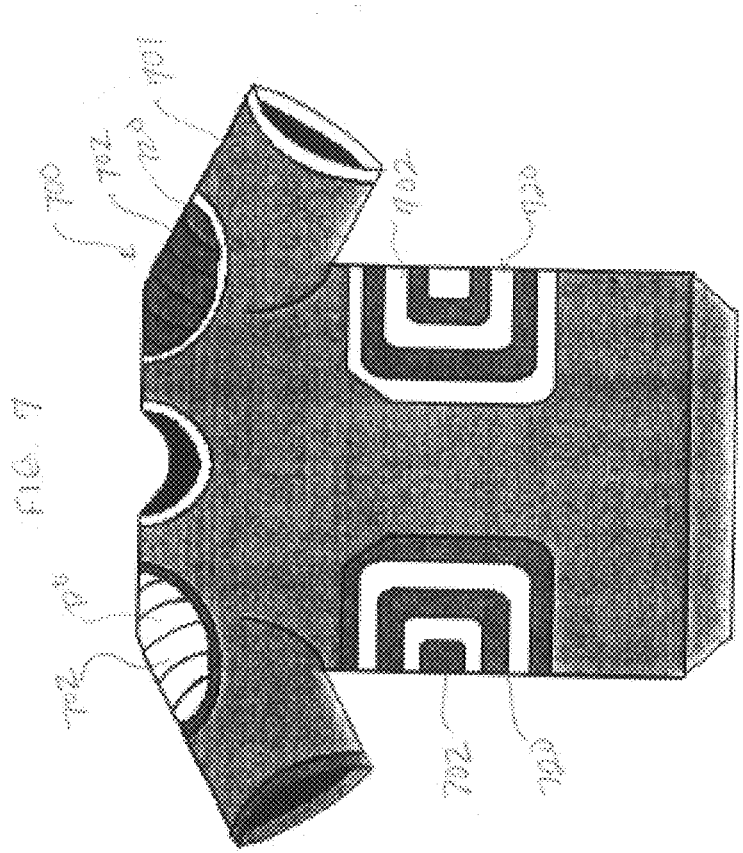

BLADDER DEVICE AND BRACE APPARATUSES COMPRISING THE BLADDER DEVICE

CROSS-REFERENCE

This is a non-provisional application claiming priority to the provisional application U.S. Application Ser. No. 61/680,700, filed Aug. 7, 2012, the contents of which are incorporated herein by reference.

BACKGROUND OF THE INVENTION

The present invention relates to a joint support device. More particularly, to a bladder device and a brace apparatus comprising the bladder device.

There are several types of brace apparatuses that are currently being used to provide joint support for specific joint regions, e.g., knees, ankles, and wrists of a user. A brace apparatus surrounds the joint region and provides a predetermined amount of joint support based on the structure of the brace apparatus. Some brace apparatuses are stretchable slip-on type brace apparatuses that surround the joint region and have problems such as providing minimal support due to an inability to be further adjusted. Other brace apparatuses have different mechanisms for performing tightening operation thereof. The latter typically include adjustable straps and/or an air pressure mechanism (e.g., a pump) to allow a user to tighten the brace apparatuses. There are some problems associated with a conventional brace apparatus including only providing pressure/support to the total joint region, thereby providing unwanted amounts of support to some portions of the joint region.

SUMMARY OF THE INVENTION

Embodiments of the present invention obviate the above-mentioned problems, by providing a bladder device able to provide varying support to one or more selected portions of the joint region as desired by a user.

According to an embodiment of the present invention, a bladder device to be inserted into a brace apparatus is provided. The bladder device comprising a body portion configured to receive air, a pump mechanism configured to pump air into the body portion; and a release mechanism configured to release air pumped into the body portion, wherein the pump mechanism and the release mechanism are operable to provide a varying amount of air into the body portion, as desired by the user.

According to another embodiment of the present invention, a brace apparatus comprising a brace portion including a flexible housing part configured to receive and secure a joint part of a user therein and comprising at least one pocket region on an interior surface thereof; and at least one bladder device configured to be inserted into the at least one pocket region, and including a body portion configured to receive air, a pump mechanism configured to pump air into the body portion, and a release mechanism configured to release air pumped into the body portion, wherein the pump mechanism and the release mechanism are operable to provide a varying amount of air into the body portion, as desired by the user, and supplying adjustable support to at least one region of the joint part as selected by the user.

According to another embodiment of the present invention, a brace apparatus comprising a brace portion including a flexible housing part configured to receive and secure a joint part of a user therein and comprising a plurality of pocket regions on an interior surface thereof; and a corresponding plurality of bladder devices configured to be inserted into the plurality of pocket regions, and each including a body portion configured to receive air, a pump mechanism configured to pump air into the body portion, and a release mechanism configured to release air pumped into the body portion, wherein the pump mechanism and the release mechanism are operable to provide a varying amount of air into the body portion, as desired by the user, and supplying adjustable support to at least one region of the joint part as selected by the user.

Other embodiments of the bladder devices and other brace apparatuses are further described below.

Additional features and advantages are realized through the techniques of the present invention. Other embodiments and aspects of the invention are described in detail herein and are considered a part of the claimed invention. For a better understanding of the invention with the advantages and features, refer to the description and to the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

FIG. 1 illustrates a bladder device that can be implemented within one or more embodiments of the present invention.

FIGS. 2A-2C are schematic views of a brace apparatus (e.g., a knee brace apparatus) including bladder devices that can be implemented within embodiments of the present invention.

FIGS. 3A-3C are schematic views of a brace apparatus (e.g., a knee brace apparatus) including bladder devices that can be implemented within alternative embodiments of the present invention.

FIGS. 4A-4C are schematic views of a brace apparatus (e.g., an arm/elbow brace apparatus) including a bladder device that can be implemented within alternative embodiments of the present invention.

FIGS. 5A-5F are schematic views of a brace apparatus (e.g., an ankle brace apparatus) including bladder devices that can be implemented within alternative embodiments of the present invention.

FIGS. 6A and 6B are schematic views of a brace apparatus (e.g., a sports girdle) including bladder devices that can be implemented within alternative embodiments of the present invention.

FIG. 7 is a schematic view of a brace apparatus (e.g., a shirt) including bladder devices that can be implemented within alternative embodiments of the present invention.

DETAILED DESCRIPTION OF THE DRAWINGS

Figure 8:
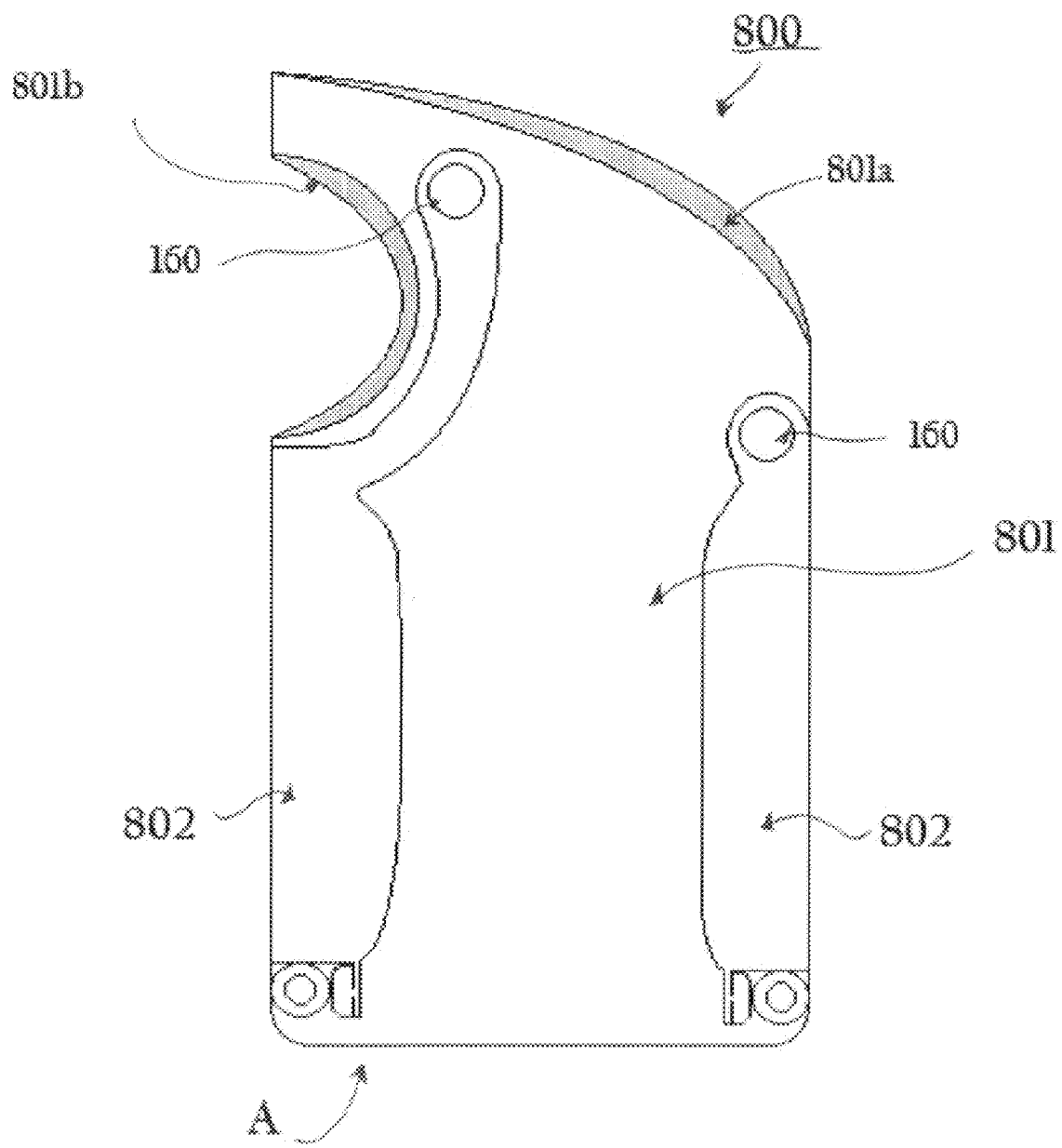
FIG. 8 is a schematic view of a brace apparatus (e.g., a wrist brace apparatus) including bladder devices as shown in FIG. 1 that can be implemented within alternative embodiments of the present invention.

Embodiments of the present invention provide bladder devices and various brace apparatuses for providing added support to joint regions of a user. Use of the bladder devices according to embodiments of the present invention, enable a user to control the amount of pressure and resulting support to be supplied to selected portions of the joint regions. For example, a user may need added pressure and support at one side (e.g., a right side) of their knee and less pressure and support to the left side of their knee. Further, according to one or more embodiments, the bladder devices are able to be inserted into existing brace apparatuses. Further, according to one or more embodiments, the bladder devices are lightweight and water-proof. In addition, cold/hot packs are also insertable into the brace apparatuses along with the bladder devices separately or integrally combined therewith, as needed to provide additional comfort and care to the joint region, as needed.

FIG. 1 illustrates a bladder device 100 that can be implemented within one or more embodiments of the present invention. The bladder device 100 is insertable into a brace apparatus (as depicted in FIG. 2A, for example). The bladder device 100 comprising a body portion 101 configured to receive air therein. The body portion 101 includes multiple pocket portions 101a through 101d for receiving the air. Air is pumped into the body portion 101 via a pump mechanism 150. A release mechanism 160 is also provided for releasing the air pumped into the body portion 101 as desired by the user. Thus, according to one or more embodiments, the pump mechanism 150 and the release mechanism 160 are operable to provide a varying amount of air into the body portion 101, as desired by the user. A pressure valve (not shown) may also be implemented to enable control and monitoring of the amount of air within the body portion 101.

According to one or more embodiments of the present invention, the pump mechanism 150 is formed at a center region of a top portion of the bladder device 100. And is surrounded by a pocket portion 101a of the body portion 101 such that the user applies pressure to the pump mechanism 150 (i.e., pressing it in) to pump air into the bladder device 100. The present invention is not limited to the pump mechanism 150 being formed of a particular shape, size or material, or being disposed in a particular location within the bladder device 100, and thus may vary as desired. Other types of pump mechanisms may be implemented within embodiments of the present invention. According to one embodiment, the pump mechanism 150 is larger than the body portion 101.

According to one or more embodiments, the release mechanism 160 is disposed within a close proximity to the release mechanism 160 and used to thereby enable the user to release air from the body portion 101 of the bladder device 100 as desired. The release mechanism 160 may be formed of any shape, size, or material. The release mechanism 160 may be of a pin structure used to alleviate air from the body portion 101 of the bladder device 100 when desired by the user.

The present invention is not limited to the use of the bladder device 100 shown in FIG. 1. Other embodiments of the bladder device will be described below with reference to FIGS. 10 through 12.

According to one or more embodiments, in the body portion 101, the pocket portions 101a through 101d and the pump mechanism 150 may be formed using a single mold during manufacturing. The pocket portions 101a through 101d are integrally combined together such that connection portions 102 are provided between each pocket portion 101a through 101d. Further, air through-holes 103 are provided at each side surface of the connection portions 102 to allow air to flow freely between the pocket portions 101a through 101d. According to other embodiments, the air though-holes 103 may be formed at a center region of the connection portions 102 or any other region along the connection portions 102. Further, according to alternative embodiments, the connection portions 102 may be omitted.

The body portion 101 further includes an insertion portion 104 for housing the release mechanism 160. According to one or more embodiments, the release mechanism 160 is insertable into the insertion portion 104 and is able to be operated to release air as needed from the body portion 101 of the bladder device 100. According to one or more embodiments, the release mechanism 160 may be removable to thereby be replaced or repaired when necessary.

According to embodiments of the present invention, the body portion 101 is not limited to being formed of multiple separate pocket portions 101a through 101d. The body portion 101 is further not limited to being formed of a particular number of pocket portions, for example, in other embodiments the body portion 101 may be formed of a single pocket portion. Further, the body portion 101 in its entirety may be formed of any shape or size as desired. Further, the pocket portions 101a through 101d may be formed of any shape or size as desired. That is, the pocket portions 101a through 101d may each be formed of a same shape or different shape from each other.

Further, according to one or more embodiments, the bladder device 100 may be formed of various types of materials. According to one or more embodiments, the bladder device 100 is formed of a plastic material, rubber material or other flexible material, or any other material suitable for the purpose set forth herein. For example, the bladder device 100 may be formed of neoprene rubber. The bladder device 100 may be integrally combined with a hot and/or cold pack to provide added comfort and support. Alternatively, according to other embodiments, the bladder device 100 may be formed of a material suitable for providing cold or heat to the joint region. That is, the bladder device 100 may service as a cold/hot pack without the need for a separate cold/hot pack.

Further, according to embodiments, the pump mechanism 150 may be formed of a same material or different material from that of the body portion 101, and thus may be integrally formed with the body portion 101. Further, according to one or more alternative embodiments, the pump mechanism 150 may be a separate device from that of the body portion 101 and connected with the body portion 101 via a connection means (not shown).

According to one or more embodiments, the release mechanism 160 may be formed of rubber, or a metal material (e.g., steel, aluminum or titanium) or any other suitable material for the purpose set forth herein. Further, the release mechanism 160 may be integrally combined with the body portion 101 and/or pump mechanism 150 according to other embodiments.

In addition, the release mechanism 160 may be formed as a separate component from the body portion 101 and the pump mechanism 150 according to other embodiments.

Further, a bladder device according to alternative embodiments will be discussed below with reference to FIGS. 10 through 12.

Figure 10:
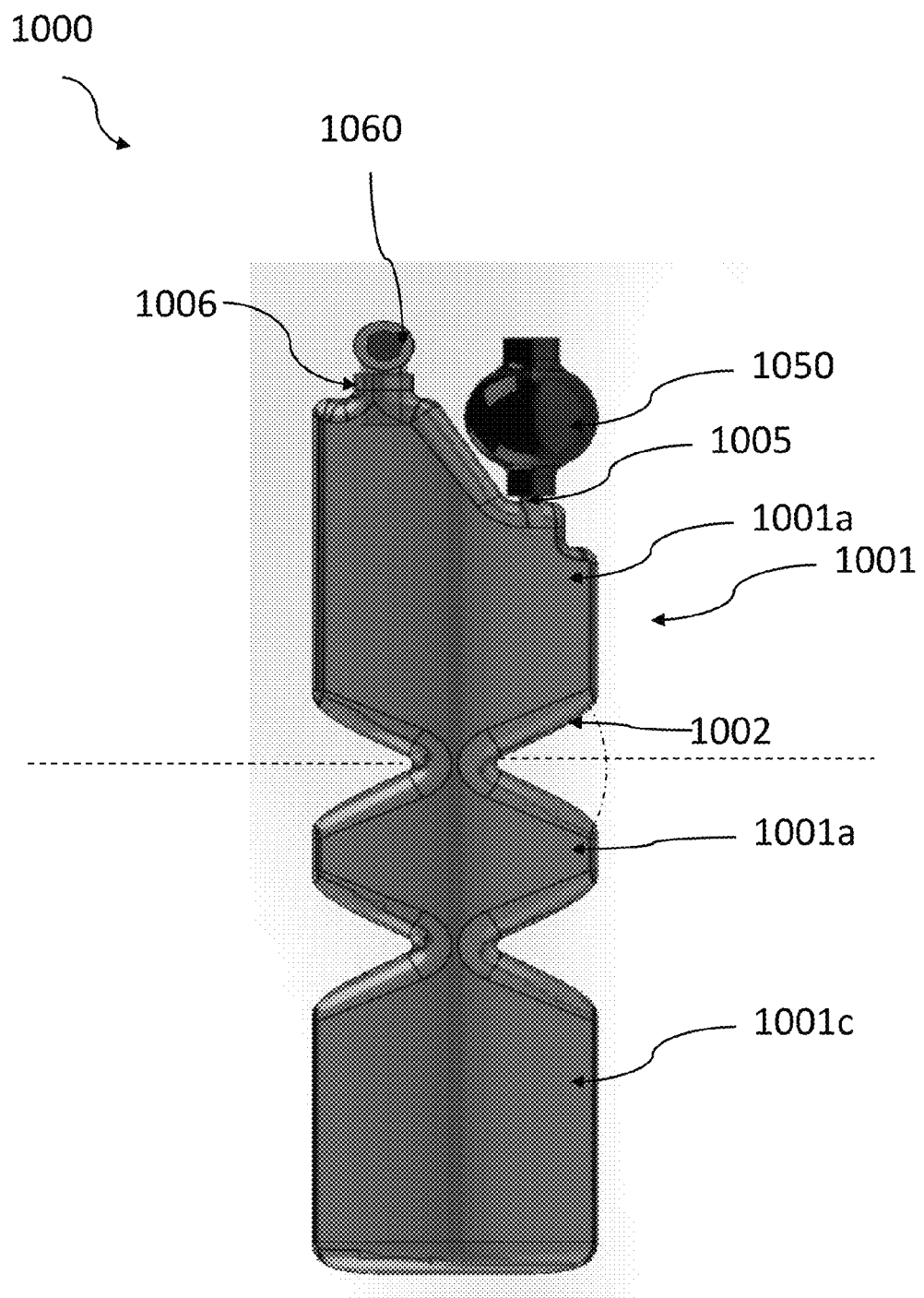
FIG. 10 is a schematic top view of a bladder device that can be implemented within alternative embodiments of the present invention.
Figure 11:
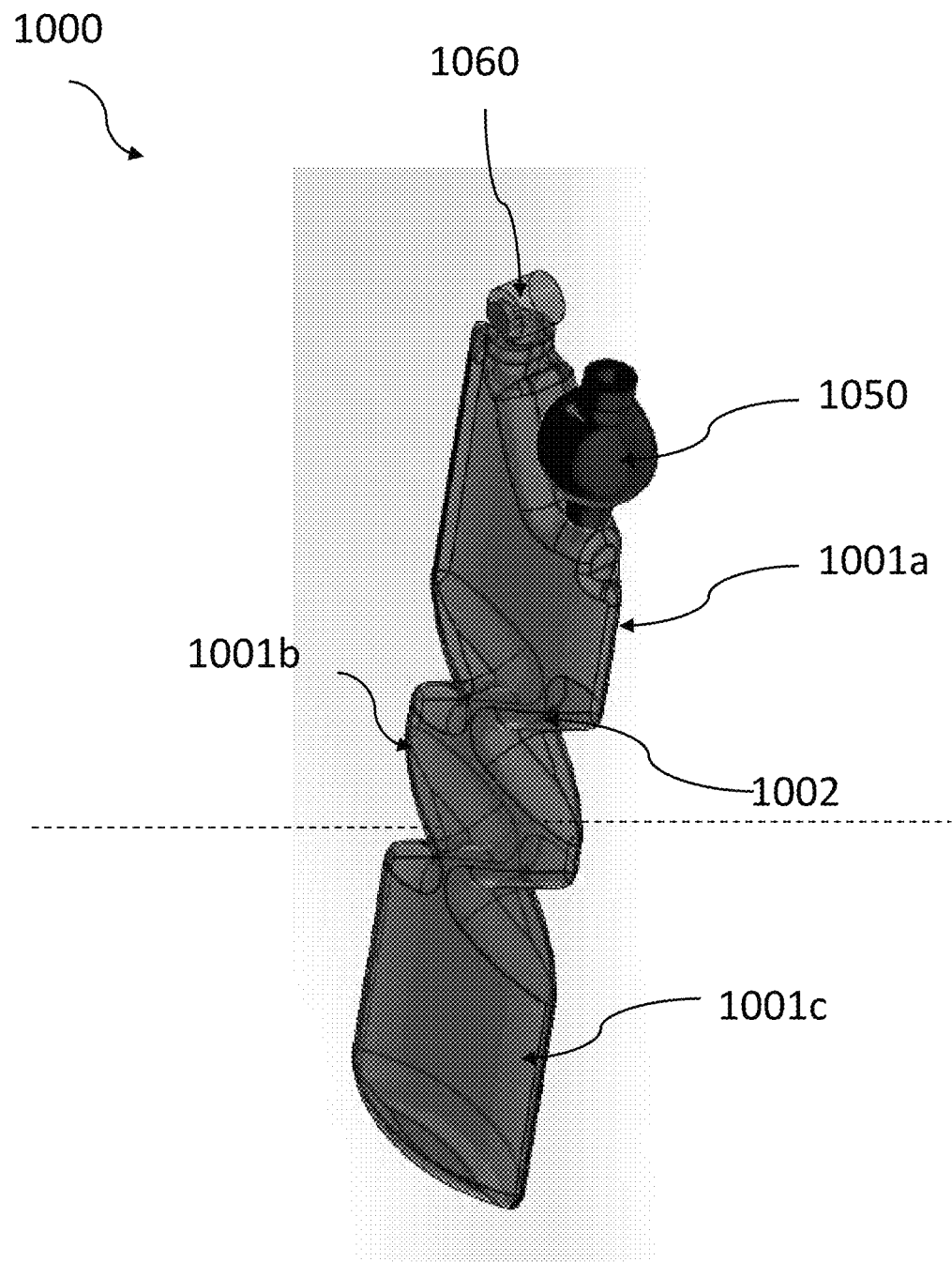
FIG. 11 is a schematic side view of the bladder device shown in FIG. 10 that can be implemented within alternative embodiments of the present invention.
Figure 12:
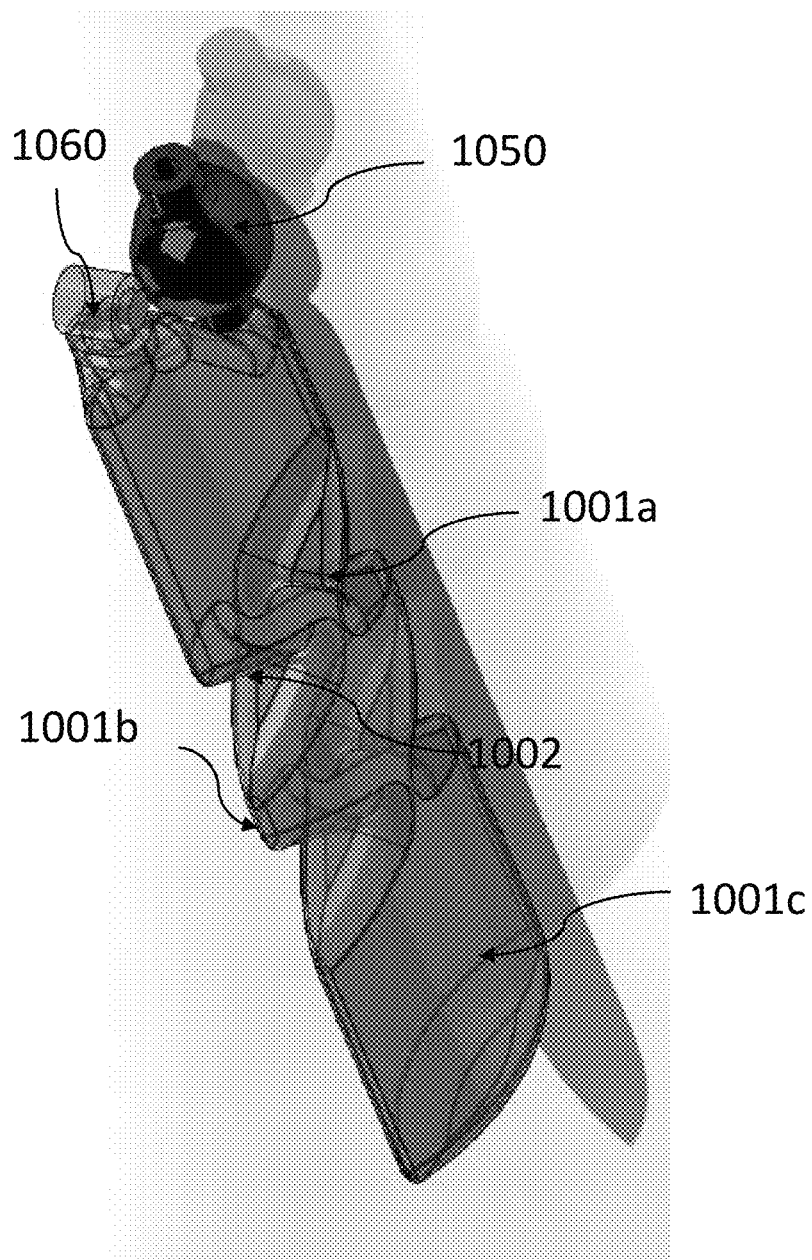
FIG. 12 is schematic view of the bladder device shown in FIGS. 10 and 11 in operation in accordance within one or more embodiments of the present invention.

Referring to FIGS. 10 through 12, a bladder device 1000 is provided. The bladder device 1000 comprises a body portion 1001 that includes at least one angled portion 1002 formed on each side of the body portion 1001. According to one embodiment, the body portion 1001 includes one or more pocket portions 1001a through 1001c for receiving air. The pocket portions 1001a through 1001c may be formed of the same shape and size, or different shapes and sizes from each other.

For example, according to one embodiment, the pocket portion 1001b may be smaller in size than the pocket portions 1001a and 1001c. Further, the pocket portion 1001a may be formed of a size larger than that of the pocket portions 1001b and 1001c.

According to one or more embodiments, each angled portion 1002 is formed of a predetermined angle, for example, approximately 22½°. According to other embodiments, the angled portions 1002 may be formed of a same degree of angle or a different degree of angle. According to an embodiment of the present invention, the degree of angle of the angled portions 1002 ranges between approximately 17 and approximately 28 degrees. However, the present invention is not limited to the angled portion 1002 being of a particular degree, and may vary accordingly. Further, the bladder device 1000 may be twisted, turned in any direction at any degree of angle as needed by the user thereof and corresponding to the user's range of motion, when worn within a brace apparatus.

The angled portions 1002 may be formed between the pocket portions 1001a through 1001c to connect the pocket portions 1001a through 1001c to each other. Thus, the angled portions 1002 enable the body portion 1001 to move in a flexible manner such that the body portion 1001 may turn from one direction to another direction at different sections thereof, as desired by the user, and/or based on the movement of the user when wearing the bladder device 1000 in a brace apparatus. For example, the body portion 1001 may bend in vertical direction and a horizontal direction, as needed. The degree of each angled portion 1002 may be specific to a desired angle of movement of the user. Thus, the angled portion 1002 closest to a joint of the user, may be larger or smaller than the angled portion 1002 at an opposite side of the body portion 1001.

The body portion 1001 including pocket portions 1001a through 1001c and the angled portions 1002 may be integrally formed together during manufacturing using a single mold process.

Further, a pump mechanism 1050 may be connected with a connection portion 1005 of the of the body portion 1001. The connection portion 1005 includes protruding portion for receiving the pump mechanism 1050 thereon. In this embodiment, the pump mechanism 150 is disposed at a top surface exterior surface of the body portion 1001 to be actuated by a user as desired. The pump mechanism 1050 functions in a similar manner as the pump mechanism 150 shown in FIG. 1.

A release mechanism 1060 is also provided and is disposed within close proximity to the pump mechanism 1050. According to an embodiment of the present invention, the release mechanism 1060 is received within a receiving portion 1006 (i.e., a through-hole) of the body portion 1001. The release mechanism 1060 functions in a similar manner as the release mechanism 160 shown in FIG. 1.

According to an alternative embodiment, the pump mechanism 150 and the release mechanism 160 may be welded to the body portion 101 during manufacturing.

As shown in FIG. 11, the body portion 1001 including the pocket portions 1001a through 1001c and the angled portions 1002 are of a predetermined thickness to be able to hold the air pumped therein. According to one or more embodiments, the thickness may range from of approximately 0.030 inches when in a flattened state to approximately 1 inch in an inflated (i.e., expanded) state. The thickness may be restricted by the degree of expansion capability of the brace apparatus since the bladder device is inserted into the a brace apparatus for operation thereof. However, the present invention is not limited to the bladder device 1000 being of any particular thickness and may vary as needed.

As shown in FIG. 12, when air is pumped into the body portion 1001, the body portion 1001 is in an expanded state and is able to be flexibly rotated about the angled portions 1002 as desired by the user and/or based on the movement of the user when wearing a brace apparatus including the bladder device 1000.

The bladder devices 100 and 1000 may be implemented within various types of brace apparatuses. Additional details regarding different types of brace apparatuses will be discussed below with reference to FIGS. 2A through 9.

FIGS. 2A-2C are schematic views of a knee brace apparatus 200 including bladder devices 100, 1000 as shown in FIGS. 1 and 10, respectively, that can be implemented within embodiments of the present invention. FIGS. 2A-2C show a front view, a side view and a rear view of knee brace apparatus 200, respectively.

As shown, the knee brace apparatus 200 includes a brace portion 201 including a flexible housing part configured to receive and secure a joint region (i.e., a knee) of a user therein.

As shown in FIGS. 2A-2C, according to one or more embodiments, the brace portion 201 (e.g., 201a and 201b) may be formed of a stretchable type of material to surround the joint region. The brace portion 201 is not limited to being formed of a particular material and may vary accordingly. Further, the front, side and rear surfaces of the brace portion 201 may be formed of a different material from each other. For example, the rear surface shown in FIG. 2c, may be formed of a more stretchable material than that of the front and side surfaces of the brace portion 201.

Further, according to an embodiment, the brace portion 201 includes pocket regions 202 on interior side surfaces thereof (as can be seen at the side portions of the brace apparatus 200). At least one bladder device 100 or 1000 as discussed above with reference to FIGS. 1 and 10 is configured to be inserted into each pocket region 202. According to one or more embodiments, each bladder device 100, 1000 corresponds to a pocket region 202. The present invention is not limited to any particular number of bladder devices 100, 1000 and pocket regions 202 being included in the brace apparatus 200.

According to one or more embodiments, the pocket regions 202 may be insertable-type regions 202, to be inserted into existing brace apparatuses via a securing mechanism such as snap-fit portions, zippers or Velcro™. Further, the pocket regions 202 may be formed of the same material or a different material than that of the brace portion 201.

An operation of the brace apparatus 200 and bladder devices 100, 1000 inserted therein will now be explained with reference to FIG. 2B.

According to the current embodiment, a user's leg 1 is inserted into the brace apparatus 200 such that he brace apparatus 200 is centered at the joint region of the leg 1 (i.e., a knee of the user). When worn, pocket regions 202 are disposed at side surfaces of the user's knee, so that the bladder devices 100, 1000 inserted therein may be used to add pressure/support to the side surfaces of a user's knee. The release mechanism 160, 1060, of each bladder device 100, 1000 extends via a through hold 202a of each pocket region 202. According to one or more embodiments, the bladder devices 100, 1000 may be integrally combined together and controlled via a single pump mechanism 150, 1050 and/or a single release mechanism 160, 1060. The user is able to provide varying amounts of air into the body portion 101, 1001 of each bladder device 100, 1000 as desired by the user, thereby supplying adjustable support to at least one region of the joint part (i.e., the knee) as selected by the user.

The present invention is not limited to only using two bladder devices 100, 1000 with a brace apparatus. FIGS. 3A-3C are schematic views of a knee brace apparatus including three bladder devices 100, 1000 that can be implemented within alternative embodiments of the present invention. FIGS. 3A-3C show a front view, a side view and a rear view of knee brace apparatus 300, respectively. Some of the elements (e.g., body portion 301, pocket regions 302, etc.) shown in FIGS. 3A-3C are the same as those shown in the knee brace apparatus 200 shown in FIGS. 2A-2C and function in a similar manner, therefore a detailed description thereof is being omitted herein to avoid unnecessary repetition of the same.

As shown in FIGS. 3A-3C in addition to the bladder devices 100, 1000 being disposed at side surfaces, the knee apparatus 300 shown in FIGS. 3A-3C further includes a pocket region 302 at a front surface 301a of the brace portion 301 for receiving and housing a bladder device 100, 1000 therein to provide added pressure/support to a front surface of the knee as needed.

The present invention is not limited to the bladder devices 100 and 1000 shown in FIGS. 1 and 10, respectively, and may be varied to correspond to different shapes and sizes of brace apparatuses as needed. Examples of types of bladder devices will be described below with reference to FIGS. 4A-7 and 9.

FIGS. 4A-4C are schematic views of an arm/elbow apparatus 400 including a bladder device 420 that can be implemented within alternative embodiments of the present invention. FIGS. 4A-4C show a front view, a side view, and a rear view of the arm/elbow brace apparatus 400, respectively. As shown, the arm/elbow brace apparatus 400 includes a brace portion 401 including a flexible housing part configured to receive an arm and elbow of a user therein. According to an embodiment of the present invention, front, side and rear portions 401a-401c of the brace portion 401 may be formed of the same or different materials. For example, the rear portion 401c may be formed of a more stretchable material than that of the front and side portions 401a and 401b. The brace portion 401 includes a cut-away portion 401a for inserting the elbow of the user therein such that the user's elbow rests in the portion 401a when the brace apparatus 400 is worn. The brace apparatus 400 further includes a pocket region 402 having a first through hole 402a and surrounding the joint region (i.e., the elbow) at the cut-away portion 401a of the brace portion 401. According to an embodiment of the present invention, the first through-hole 402a of the pocket region 402 is aligned with the cut-away portion 401a of the brace portion 401 so that the elbow of the user can be inserted therethrough.

As shown, according to one or more embodiments, the pocket region 402 is formed in an H-shape. The present invention is not limited to the pocket region 402 being formed of a particular shape. The pocket region 402 may be formed of a V shape, U shape, or any other shape suitable to provide arm/elbow support.

According to an embodiment of the invention, a bladder device 420 is provided and is formed of a same shape as that of the pocket region 402. The bladder device 420 is inserted into the pocket region 402 such that the release mechanism 160 thereof extends through a second through-hole 402b of the pocket region 402. In operation, the bladder device 420 is pumped via its pump mechanism 150 to provide support to the arm/elbow of the user. The user is able to adjust the amount of air therein by using the release mechanism 160. Although the bladder device 420 is formed as a single bladder, according to other embodiments of the present invention, the bladder device 420 may be formed as two or more separate bladders, for example, similar to bladder devices 100, 1000 shown in FIGS. 2A-3C and 10-12 and operated via separate pump mechanisms 150, 1050 and release mechanism 160, 1060 to provide varying support to the user at selected portions of the arm/elbow region, as desired.

FIGS. 5A-5F are schematic views of an ankle brace apparatus 500 including bladder devices 520 that can be implemented within alternative embodiments of the present invention. FIGS. 5A-5C show a front view, a side view, and a rear view of the ankle brace apparatus 500, respectively. Further, FIG. 5D shows a release mechanism 160 of a bladder device 520; and FIGS. 5E and 5F show internal and external views of the bladder device 520.

As shown in FIGS. 5A-5C, the ankle brace apparatus 500 includes a brace portion 501 including a flexible housing part configured to receive an ankle of a user therein. The brace portion 501 is formed to surround the ankle of the user and includes a first through-hole 501a (see FIG. 5A) for receiving a front portion of the user's foot and a second through-hole 501b (see FIG. 5C) for receiving a back portion of the user's foot. The brace portion 501 includes saddle-shaped pocket regions 502 for receiving bladder devices 520 (as depicted in FIGS. 5E and 5F discussed below). The pocket regions 502 are not limited to any particular shape or size and may vary accordingly. The pocket regions 502 are formed at each side of the brace portion 501 and each include a through-hole 602a for receiving a release mechanism 160 of each bladder device 520. The pump mechanism 150 (as shown in FIG. 5F, for example) of each bladder device 520 rests in a center region 502b of the pocket region 502 when inserted therein, to allow a user to initiate air flow into the bladder device 520. The air flow is able to be pumped and released as desired via the respective pump and release mechanisms 150 and 160 of the bladder devices 520.

According to one or more embodiments, the bladder devices 520 may be integrally combined as a single unit and operable via a single pump mechanism 150 and release mechanism 160 or operable via separate pump and release mechanisms 150 and 160 as shown in FIGS. 5A-5C.

Additional details regarding the bladder devices 520 will now be discussed with reference to FIGS. 5E and 5F. As shown in FIG. 5E, the interior of the bladder device 520 is formed of plastic or rubber for example, or any other suitable material. Further, as shown in FIG. 5F, the exterior of the bladder device 520 may be formed of a rubber or plastic material, or any other suitable material for the purpose set forth herein.

FIGS. 6A and 6B are schematic views including a side view and a rear view of a girdle 600 e.g., a sports girdle including bladder devices 620 and 630 that can be implemented within alternative embodiments of the present invention. The present invention is not limited to being used within sports girdles and may be used with any type of girdle providing hip, thigh, lower back and/or abdominal support as needed, e.g., as a medical-type surgical support girdle.

The girdle 600 includes a brace portion 601 having front, side and rear surfaces 601a-601c. As shown in FIG. 6A, the girdle 600 includes pocket regions 602 on an interior side surface of the girdle 600. The pocket regions 602 include a first through-hole 602a for receiving a pump mechanism 150 of each bladder device 620 and a second through-hole 602b for receiving a release mechanism 160 of the bladder device 620.

Each bladder device 620 includes pocket portions 620a-620c extending along an entire side surface 601b of the brace portion 601 of the girdle 600. According to one or more embodiments, the bladder device 620 is not limited to including a particular number of pocket portions 620a-620c for receiving air pumped via the pump mechanism 150. Further, the bladder device 620 and the pocket portions 620a-620c thereof may be formed in a similar manner as the body portion 101 and the pocket portions 101a-101d of the bladder device 100 (see FIG. 1) or the body portion 1001 and the pocket portions 1001a-1001c of the bladder device 1000 (see FIG. 10). The bladder device 620 may be formed to extend along a predetermined width of the user's side to provide more or less support as needed. As shown, the center pocket 620b is formed of a circular shape in FIG. 6B, however the pocket portions mentioned above are not limited to any particular shape and may vary as needed.

Although not illustrated, the girdle 600 may also include bladder devices 630 and pocket regions 602 at a front surface thereof.

Further, as shown in FIG. 6B, a bladder device 630 may be provided at a rear surface 601 of the brace portion 601 in accordance with other embodiments of the present invention. As shown, the bladder device 630 is formed in a T-shape across a rear portion 601c of the brace portion 601. According to embodiments, the bladder device 630 may include one or more pump mechanism 150 and one or more release mechanisms 160. In operation, air is pumped into a back portion of the brace portion 601 to provide added support in a rear end area of the user. The present invention is not limited to the bladder device 630 being formed of a particular shape or size and may vary as needed.

FIG. 7 is a schematic view of a shirt 700 including bladder devices 720 that can be implemented within alternative embodiments of the present invention. According to an embodiment of the present invention, the shirt 700 may be a sport shirt used for football or rugby, for example or any other sport requiring additional padding and support in the chest, abdomen and shoulder areas. The shirt 700 includes a shirt portion 701 having one or more pocket regions 702 formed at shoulder regions and side regions including, for example, front abdominal and back regions. The bladder devices 720 may be formed similar to the bladder devices shown in FIGS. 1 through 6C and 10. The bladder devices 720 are insertable into the pocket regions 702 such that a pump mechanism 150 (not shown) is positioned in a region (e.g., a center region) of each pocket region 702 and the release mechanism 160 (not shown) are operable by the user to supply air into and release air from the respective bladder devices 720. According to one or more embodiments, the bladder devices 720 are operable via separate pump and release mechanisms 150 and 160 or two or more bladder devices 720 are combined together to be operable via single pump and release mechanisms 150 and 160.

According to other embodiment of the present invention, pockets 702 and corresponding bladder devices 720 may be provided at various locations on the shirt 700 to provide support when desired. As mentioned above, according to embodiments, the pockets 702 are insertable and attachable to an interior of the shirt 700 via a securing means such as Velcro™. Therefore, the bladder devices 720 may be inserted in any places within the shirt 700, as desired by the user.

FIG. 8 is a schematic view of a wrist brace apparatus 80 including bladder devices 820 similar to bladder devices 100, 1000 shown in FIGS. 1 and 10, respectively that can be implemented within alternative embodiments of the present invention.

As shown in FIG. 8, the wrist brace apparatus 800 includes a body portion 801 formed of a stretchable material, for example, to receive a user's wrist and thumb portion therein via through-holes 801a and 801b, respectively (see arrow A). The wrist brace apparatus 800 further includes pocket regions 802 for receiving bladder devices 820 therein. Similar to the bladder devices 100, 1000, the bladder devices 820 allow a user to pump air into and release air therefrom via a pump mechanism 150 and a release mechanism 160. The bladder devices 820 may be integrally combined as a single unit or separate as shown in FIG. 8. Further, the bladder devices 820 may be operable via separate pump and release mechanisms 150 and 160, or single pump mechanism 150 and a single release mechanism 160, if integrally combined.

Figure 9:
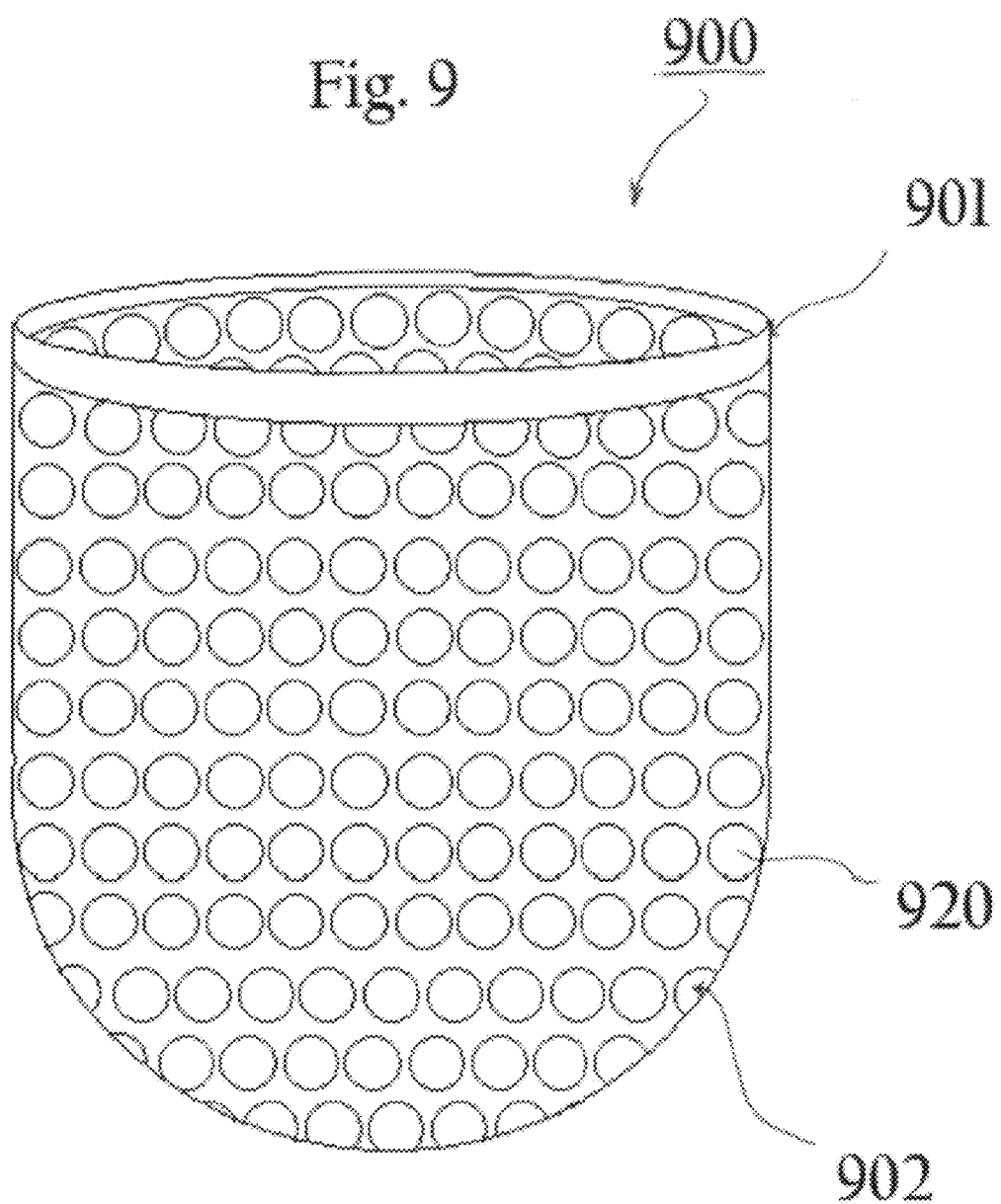
FIG. 9 is a schematic view of a brace apparatus (e.g., a cap) including bladder devices that can be implemented within alternative embodiments of the present invention.

FIG. 9 is schematic view of a cap 900 including bladder devices 920 that can be implemented within alternative embodiments of the present invention. In some sports activities e.g., cycling, rollerskating, football, rugby, and equestrian activities, helmets are required to be worn. The cap 900 may be used in conjunction with a helmet to provide added support to the head region of the user. The cap 900 may be used separately or integrally combined with the helmet.

According to one or more embodiments, the cap 900 includes one or more pocket regions 902 for receiving one or more bladder devices 920. For example, the cap 900 may include pocket regions 902 corresponding to respective sides of the head of the user, for example, a separate pocket region 902 may be provided at a front, side surfaces, top and rear surfaces of the cap 900 and therefore may receive separate bladder devices 920 therein, to provide added pressure/support where desired. According to one or more embodiments, the bladder devices 920 may be controlled via separate or same pump and release mechanism 150 and 160.

According to other embodiments, the cap 900 may include a single pocket region 902 for receiving a single bladder device 920 to supply air uniformly throughout the cap 900 as desired by the user.

Use of the bladder devices accordingly to various embodiments of the present invention provide support/pressure to joint regions and other regions of the body of a user as desired by the user. Further, the amount of support/pressure is adjustable as needed. In addition, the bladder devices are insertable into existing brace apparatuses and may provide cold/heat for added comfort and care to the user.

According to alternative embodiments, the bladder devices of the present invention could be implemented with weight belts to provide added pressure to desired areas of the user, and any type of apparel to be worn by a user. Further, although the bladder devices are shown inserted into pocket regions on an interior of various brace apparatuses illustrated herein; alternatively, the pocket regions may be formed on an exterior of the brace apparatus and the bladder devices may be inserted therein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A bladder device to be inserted into a brace apparatus comprising:
   a body portion configured to receive air; said body portion comprising a plurality of pocket portions, said plurality of pocket portions connected with each other and configured to receive air pumped therein, one or more angled portions formed between said plurality of pockets portions of the body portion, to connect the plurality of pocket portions to each other and facilitate a bending operation of the bladder device, wherein the body portion is configured to turn from one direction to another direction at different sections thereof as desired by a user or based on a movement of the user when wearing the bladder device within the brace apparatus
   a pump mechanism configured to pump air into the body portion, the pump mechanism being formed at a center region of the body portion such that the pump mechanism is surrounded by the body portion; and
   a release mechanism configured to release air pumped into the body portion, wherein the pump mechanism and the release mechanism are operable by providing a varying amount of air into the body portion, as desired by the user to adjust applied pressure to a joint part of the user.

2. The bladder device of claim 1, wherein the body portion further comprises:
   one or more connection portions between each pocket portion; and
   one or more air through-holes at each side surface of the connection portion to allow air to flow freely between the pocket portions.

3. The bladder device of claim 1, wherein the one or more angled portions are formed of a same degree of angle or a different degree of angle.

4. The bladder device of claim 3, wherein the plurality of pocket portions and the one or angled portions may be integrally formed together during manufacturing using a single mold process.

5. The bladder device of claim 4, wherein when air is pumped into the body portion, the body portion is in an expanded state and to be flexibly rotated about the one or more angled portions based on the movement of the user.

6. The bladder device of claim 1, wherein the release mechanism and the pump mechanism are integrally combined with the body portion.

7. The bladder device of claim 2, the body portion further comprises:
   a connection portion including a protruding portion for receiving the pump mechanism thereon; and
   a receiving portion within close proximity to the connection portion, for receiving the release mechanism therein.

8. A brace apparatus comprising:
   a brace portion including a flexible housing part configured to receive and secure a joint part of a user therein and comprising a plurality of pocket regions on an interior surface thereof; and
   a plurality of bladder devices configured to be inserted into said plurality of pocket regions, and including:
   a body portion configured to receive air,
   a pump mechanism configured to pump air into the body portion, the pump mechanism being formed at a center region of the body portion such that the pump mechanism is surrounded by the body portion, and
   a release mechanism configured to release air pumped into the body portion, wherein the pump mechanism and the release mechanism are operable to provide a varying amount of air into the body portion, as desired by the user, and supplying adjustable support to at least one region of the joint part as selected by the user.

9. The brace apparatus of claim 8, wherein the brace apparatus is for at least one of joint part of the user comprising: a knee, arm, elbow, ankle, wrist, head, chest, abdominal area, shoulders, waist, hips and thighs of the user and conforms to a shape of the joint part of the user.

10. The brace apparatus of claim 9, wherein the plurality of bladder devices are formed of a material for providing cold or heat to the joint part.

11. A brace apparatus comprising:
    a brace portion including a flexible housing part configured to receive and secure a joint part of a user therein and comprising:
    a plurality of pocket regions on an interior surface thereof; and
    a corresponding plurality of bladder devices configured to be inserted into the plurality of pocket regions, and each including:
    a body portion configured to receive air, a pump mechanism configured to pump air into the body portion, the pump mechanism being formed at a center region of the body portion such that the pump mechanism is surrounded by the body portion, and
    a release mechanism configured to release air pumped into the body portion, wherein the pump mechanism and the release mechanism are operable to provide a varying amount of air into the body portion, as desired by the user, and supplying adjustable support to at least one region of the joint part as selected by the user.

* * * * *